(12) United States Patent
Kamphus et al.

(10) Patent No.: US 8,076,530 B2
(45) Date of Patent: Dec. 13, 2011

(54) ABSORBENT ARTICLE WITH WATER-ABSORBING AGENT OR AGENTS

(75) Inventors: Juliane Kamphus, Schwalbach (DE); Hiroyuki Ikeuchi, Himeji (JP); Shigeru Sakamoto, Himeji (JP); Sayaka Machida, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 422 days.

(21) Appl. No.: 12/324,164

(22) Filed: Nov. 26, 2008

(65) Prior Publication Data

US 2009/0157027 A1   Jun. 18, 2009

(30) Foreign Application Priority Data

Dec. 12, 2007   (JP) ................. 2007-321228

(51) Int. Cl.
*A61F 13/15* (2006.01)
*A61F 13/20* (2006.01)

(52) U.S. Cl. ............... 604/367; 604/365; 604/358

(58) Field of Classification Search .......... 604/365, 604/367, 385.23
See application file for complete search history.

(56) References Cited

U.S. PATENT DOCUMENTS

| | | |
|---|---|---|
| 3,661,875 A | 5/1972 | Sieja |
| 3,860,003 A | 1/1975 | Buell |
| 3,935,099 A | 1/1976 | Weaver et al. |
| 3,959,569 A | 5/1976 | Burkholder, Jr. |
| 4,076,663 A | 2/1978 | Masuda et al. |
| 4,093,776 A | 6/1978 | Aoki et al. |
| 4,124,748 A | 11/1978 | Fujimoto et al. |
| 4,190,563 A * | 2/1980 | Bosley et al. .......... 523/111 |
| 4,389,513 A | 6/1983 | Miyazaki et al. |
| 4,541,871 A | 9/1985 | Obayashi et al. |
| 4,587,308 A | 5/1986 | Makita et al. |
| 4,610,678 A | 9/1986 | Weisman et al. |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,734,478 A | 3/1988 | Tsubakimoto et al. |
| 4,834,735 A | 5/1989 | Alemany et al. |
| 4,911,860 A * | 3/1990 | Van Den Brom .......... 510/283 |
| 4,940,464 A | 7/1990 | Van Gompel et al. |
| 5,098,775 A * | 3/1992 | Harada et al. .......... 442/261 |
| 5,140,076 A | 8/1992 | Harada et al. |
| 5,151,092 A | 9/1992 | Buell et al. |
| 5,164,459 A | 11/1992 | Kimura et al. |
| 5,250,640 A | 10/1993 | Irie et al. |
| 5,260,345 A | 11/1993 | DesMarais et al. |

(Continued)

FOREIGN PATENT DOCUMENTS

EP   456136 B1   3/2002

(Continued)

*Primary Examiner* — Leslie Deak
*Assistant Examiner* — Susan Su
(74) *Attorney, Agent, or Firm* — Andrew A Paul; John P. Colbert (57) ABSTRACT

An absorbent article comprising an absorbent core, which comprises a primary water-absorbing agent that can serve as a acquisition and preferably temporarily storage material for fluids, such as urine, and that has a CRC of up to 20 g/g and that comprises a compound that includes a constitutional unit derived from polyalkyleneglycol and that is other than an unsaturated monomer and that comprises a polyvalent metal salt. The absorbent article is preferably an infant (toddler, baby) diaper, including training pant, or adult incontinent article (e.g. a pad, diaper).

13 Claims, 2 Drawing Sheets

U.S. PATENT DOCUMENTS

| | | | | |
|---|---|---|---|---|
| 5,271,847 A | * | 12/1993 | Chen et al. | 210/697 |
| 5,275,773 A | | 1/1994 | Irie et al. | |
| 5,387,207 A | | 2/1995 | Dyer et al. | |
| 5,397,316 A | | 3/1995 | LaVon et al. | |
| 5,409,771 A | | 4/1995 | Dahmen et al. | |
| 5,554,145 A | | 9/1996 | Roe et al. | |
| 5,569,234 A | | 10/1996 | Buell et al. | |
| 5,625,222 A | | 4/1997 | Yoneda et al. | |
| 5,724,915 A | * | 3/1998 | Ochi et al. | 119/173 |
| 5,836,929 A | * | 11/1998 | Bewick-Sonntag et al. | 604/368 |
| 5,856,415 A | * | 1/1999 | Lagace et al. | 526/192 |
| 5,985,944 A | * | 11/1999 | Ishizaki et al. | 521/64 |
| 6,004,306 A | | 12/1999 | Robles et al. | |
| 6,071,976 A | | 6/2000 | Dairoku et al. | |
| 6,150,469 A | | 11/2000 | Harada et al. | |
| 6,228,930 B1 | | 5/2001 | Dairoku et al. | |
| 6,254,990 B1 | | 7/2001 | Ishizaki et al. | |
| 6,297,319 B1 | * | 10/2001 | Nagasuna et al. | 525/96 |
| 6,444,747 B1 | * | 9/2002 | Chen et al. | 524/807 |
| 6,559,239 B1 | | 5/2003 | Riegel et al. | |
| 6,641,754 B2 | * | 11/2003 | Buentello et al. | 252/180 |
| 7,183,456 B2 | * | 2/2007 | Hatsuda et al. | 604/372 |
| 7,638,570 B2 | * | 12/2009 | Torii et al. | 524/430 |
| 7,744,576 B2 | * | 6/2010 | Busam et al. | 604/385.101 |
| 7,825,169 B2 | * | 11/2010 | Wada et al. | 523/102 |
| 2004/0167486 A1 | * | 8/2004 | Busam et al. | 604/367 |
| 2004/0254553 A1 | * | 12/2004 | Fujimaru et al. | 604/372 |
| 2005/0118423 A1 | * | 6/2005 | Adachi et al. | 428/402 |
| 2005/0209352 A1 | * | 9/2005 | Dairoku et al. | 521/50 |
| 2005/0222547 A1 | * | 10/2005 | Beruda et al. | 604/368 |
| 2007/0202772 A1 | | 8/2007 | Ikeuchi et al. | |
| 2009/0029044 A1 | * | 1/2009 | Daniel et al. | 427/195 |
| 2009/0036855 A1 | * | 2/2009 | Wada et al. | 604/372 |
| 2010/0105810 A1 | * | 4/2010 | Sakamoto et al. | 524/3 |

FOREIGN PATENT DOCUMENTS

| | | |
|---|---|---|
| EP | 1928511 A1 | 6/2008 |

* cited by examiner

ABSORBENT ARTICLE WITH WATER-ABSORBING AGENT OR AGENTS

FIELD OF THE INVENTION

The present invention relates to an absorbent article comprising an absorbent core, which comprises a primary water-absorbent agent that can serve as a acquisition and preferably temporarily storage material for fluids, such as urine, and that has a CRC of up to 20 g/g and that comprises a compound that includes a constitutional unit derived from polyalkyleneglycol and that is other than an unsaturated monomer and that comprises a polyvalent metal salt. The absorbent article is preferably an infant (toddler, baby) diaper, including training pant, or adult incontinent article (pad, diaper).

BACKGROUND TO THE INVENTION

There have been continuous investigations to provide improved absorbent article with so-called super-absorbing material (or: water-absorbing material or water-gelling material). Typically such articles and super-absorbing materials need to have a high liquid absorption rate, absorption amount and excellent retention. The super-absorbing materials are typically used in addition to fibrous materials such as cellulose fiber, polyester fiber, polyethylene fiber, and/or polypropylene fiber, which provide a structure for the super-absorbing materials or additional performance properties, other than liquid storage. For realization of thinner absorbent articles, it is desired that the absorbent fiber materials are replaced with super-absorbing materials.

As such, as a water-absorbing resin that functions like the fibrous materials in the conventional absorbent structures is desirable; e.g. water-absorbing resins that including rapidly absorbing an aqueous liquid, diffusing the aqueous liquid after having absorbed it; and (only) temporarily retaining the aqueous liquid after having absorbed it.

The present invention provides absorbent articles comprising such an improved water-absorbing agent that may replace absorbent cellulose fibrous materials, having a limited fluid retention capacity, for use in particular in acquisition/storage layers of an absorbent article.

SUMMARY OF THE INVENTION

An absorbent article comprising an absorbent core, which comprises a primary water-absorbing agent, comprising water-absorbing resin particles obtained by polymerizing an acid group-containing unsaturated monomer, said primary water-absorbing agent having a Centrifuge Retention Capacity (CRC) from 5 to 20 g/g, and said agent comprising (i) a compound that includes a constitutional unit derived from polyalkyleneglycol and that is other than an unsaturated monomer; and (ii) a polyvalent metal salt.

The absorbent article is preferably a disposable absorbent article, preferably selected from sanitary napkins, panty-liners, adult incontinence articles, including pads and diapers, and preferably infant (i.e. baby, toddler) diapers, including training pants.

The absorbent article preferably comprises a topsheet, backsheet and therein between an absorbent core, that may comprise one or more acquisition/storage layers, being in close proximity or in contact with the topsheet, and there underneath one or more storage layers, whereby at least one of the layers, typically at least one, or one, is an acquisition/storage layer and comprises the primary water-absorbing agent herein; said layer(s) may comprise preferably less than 10% by weight (of the primary water-absorbing agent in said layer) of cellulose fibers (including modified cellulose fibers such as chemically or mechanically modified cellulose fibers).

The SFC of the primary water-absorbing agent may for example be up 4000 $cm^3 \cdot s \cdot 10^{-7}/g$, or up to 3000 $cm^3 \cdot s \cdot 10^{-7}/g$, or up to 2000 $cm^3 \cdot s \cdot 10^{-7}/g$, or up to 1500 $cm^3 \cdot s \cdot 10^{-7}/g$.

The absorbent core preferably also comprises a secondary water-absorbing agent, e.g. which is chemically different to the primary water-absorbing agent, having typically a CRC of more than 20 g/g and for example a SFC of less than 600 $cm^3 \cdot s \cdot 10^{-7}/g$, or less than 400 $cm^3 \cdot s \cdot 10^{-7}/g$, but preferably an SFC of more than 50 $cm^3 \cdot s \cdot 10^{-7}/g$, or more than 80 $cm^3 \cdot s \cdot 10^{-7}/g$, or more than 100 $cm^3 \cdot s \cdot 10^{-7}/g$. The secondary water-absorbing agent may be comprised in the same layer of the absorbent core as the primary water-absorbing agent, or in one embodiment herein, it is comprises in a different layer, e.g. the storage layer or layers; whereby at least a storage layer and an acquisition/storage layer are each preferably substantially free of cellulose fibers, e.g. comprising each less than 10% by weight (of all (i.e. primary and/or secondary) water-absorbing agents present in said layer) of cellulose fibers.

In one embodiment herein it is thus preferred that said compound is present without forming a chemical bond with the water-absorbing resin particles and/or that said compound is separable from the water-absorbing resin particles.

Alternatively, or in addition, it may be preferred that said polyvalent metal salt, described hereinafter, is present without forming a chemical bond with the water-absorbing resin particles and/or that said polyvalent metal salt is separable from the water-absorbing resin particles. The absorbent article, preferably infant diaper, herein is preferably very thin, having preferably a maximum dry caliper in the crotch region (as measured herein) of 4.5 mm or less.

The disposable absorbent article herein comprises preferably an absorbent core, comprising at least said primary water-absorbing agent and optionally said secondary water-absorbing agent, and said core having one or more layers, or regions thereof, with an average density greater than about 0.2 $g/cm^3$, or said core as a whole having such a density.

DETAILED DESCRIPTION

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers (adult and infant; including training pants), adult incontinence briefs, diaper holders and liners, sanitary napkins, panty-liners and tampons.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Layer" when sued herein as a layer of an absorbent core refers to a three dimensional structure with a x dimension width, y dimension length, and z-dimensions thickness or caliper, said x-y dimensions being substantially in the plane of the article. Said "layer" has at least a 2 cm×2 cm x-y dimension, preferably at least 2 cm×4 cm.

"Region", when used herein as a region of an absorbent core or layer thereof, means herein an area (with when applicable a z-direction caliper, for example being less than 4.5 mm, as defined herein) of 2 cm×2 cm.

"Water-absorbing" when used herein includes compounds, materials, products that absorb at least water, but typically also other aqueous fluids, and typically at least urine, or blood.

The absorbent articles envisaged herein comprise a supporting structure and the primary water-absorbing agent described herein. A preferred absorbent article herein preferably comprises a topsheet and a backsheet, described herein below, with therein between an absorbent core, comprising said primary water-absorbing agent. A preferred article herein is a baby or infant diaper, an adult incontinent product (pad or diaper), or sanitary napkin or panty-liner, which comprises a chassis, which comprises a topsheet and a backsheet, for example a liquid pervious topsheet and a liquid impervious backsheet.

The chassis may further include side panels, (elasticized) leg cuffs and/or barrier cuffs, and/or an (elastic) waist feature. One end portion of the article is configured as a first waist region of the article. The opposite end portion is configured as a second waist region. An intermediate portion is configured as a crotch region, which extends longitudinally between the first and second waist regions. The crotch region is that portion which, when the article is worn, is generally positioned between the wearer's legs. The average length of the crotch portion is ⅓ of the average length of the article, being the centre ⅓ of the article, in longitudinal direction.

The chassis may also comprise a fastening system, which may include at least one fastening member and at least one landing zone.

For unitary absorbent articles like diapers, the chassis comprises the main structure of the diaper with other features added to form the composite diaper structure. While diaper may be assembled in a variety of well-known configurations, preferred diaper configurations are described generally in U.S. Pat. Nos. 4,940,464, 5,554,145; 5,569,234; 6,004,306, U.S. patent application Ser. No. 10/171,249 and in U.S. patent application Ser. No. 10/824,121.

The topsheet is compliant, soft feeling, and non-irritating to the wearer's skin. It may be liquid pervious, permitting liquids to readily penetrate through its thickness. A suitable topsheet can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. In one embodiment, the topsheet is made of a hydrophobic material to isolate the wearer's skin from liquids in the absorbent core, and it may then comprise one or more opening to receive the bodily exudates. Preferably the topsheet comprises a means to adjust hydrophilicity of the material, like a surfactant. A preferred topsheet comprises a nonwoven material made using means well known to those skilled in the fabrics art. Preferably, the topsheet has a basis weight from about 10 to about 25 g/m², a minimum dry tensile strength of at least about 150 g/cm in the machine direction and a strikethrough of less than about 3 seconds according to European Disposables and Nonwovens Association standard method 150.4-99. One suitable topsheet comprises a polypropylene spunbonded nonwoven comprises fibers of less than 3 denier having a basis weight of about 18 g/m² as is available from BBA Fiberweb of Simpsonville, S.C.

The backsheet is preferably joined to the topsheet at least about a portion of the periphery thereof. The backsheet prevents exudates absorbed by the absorbent core and contained within the article from soiling other external articles that may contact the article, such as bed sheets and clothing. The backsheet is preferably manufactured from a thin polymer film. In one preferred embodiment the film is impervious to liquids. Typically, the backsheet comprises a layer of polyethylene film having a basis weight between about 10 g/m² and about 30 g/m², although other flexible, liquid impervious materials can be used. Preferably, the film is breathable (e.g., via micropores) so as to permit vapors to escape from the diaper while still preventing exudates from passing through the backsheet. Particularly preferred backsheet materials have a nonwoven laminated to the film layer so as to make backsheet more "cloth-like". Such a nonwoven layer may comprise a nonwoven material (e.g., one having a spunbonded or other suitable structure) with a basis weight between about 15 g/m² and about 25 g/m². Suitable materials for use as backsheet are available form Clopay Plastic Products Company of Mason, Ohio. Additional features for absorbent articles are well known in the art and are e.g., described in U.S. Pat. No. 3,860,003 and U.S. Pat. No. 5,151,092.

The absorbent article herein typically comprises an absorbent core, comprising or at least one layer that comprises the primary water-absorbing agent described herein. Exemplary absorbent structures or cores for use herein are described in U.S. Pat. Nos. 4,610,678; 4,834,735; 5,260,345; 5,387,207; 5,397,316; and 5,625,222.

The absorbent core may comprise one or more than one layers, for example at least one acquisition/storage layer, preferably in close proximity or in contact with the topsheet, and preferably at least one storage layer, in contact with or close proximity to the backsheet. Preferably both said acquisition/storage layer, comprising the primary water-absorbing agent, and said storage layer, comprising said secondary water-absorbing agent are present in the absorbent core. In a preferred embodiment, the absorbent article comprises said acquisition/storage layer and said storage layer, but it does not comprise an additional acquisition layer comprising cellulose material, or no additional acquisition layer. If the absorbent core comprises an additional acquisition layer it typically is positioned underlying the topsheet and then said acquisition/storage layer(s), mentioned above, is typically disposed between said acquisition layer and the remaining layer(s) of core, e.g. said storage layer.

Such an acquisition/storage layer, as used herein, provides acquisition along with distribution and temporarily storage of acquired fluids and optionally permanent storage of a portion thereof; such a storage layer, as used herein, provides the majority (e.g. more than 60% of the capacity) of the storage capacity of the article.

The absorbent core comprises the primary water-absorbing agent described herein below in detail, and it may comprise in addition a secondary water-absorbing agent, e.g. which is chemically different, and typically has a CRC of more than 20 g/g, preferably at least 25 g/g or preferably at least 30 g/g or even preferably at least 35 g/g. It may have a SFC of for example less than 600 cm$^3$·s·10$^{-7}$/g, preferably less than 400 cm$^3$·s·10$^{-7}$/g or even preferably less than 200 cm$^3$·s·10$^{-7}$/g, and typically at least 40 cm$^3$·s·10$^{-7}$/g, or preferably at least 80 cm$^3$·s·10$^{-7}$/g, and preferably at least 100 cm$^3$·s·10$^{-7}$/g or even at least 120 cm$^3$·s·10$^{-7}$/g.

The secondary water-absorbing agent comprises preferably secondary water-absorbing resin particles, that are obtained by polymerizing an acid group-containing unsaturated monomer, internally cross-linking said polymers and surface-cross-linking said polymers, by use of one or more crosslinking agents. However, the secondary water-absorbing agent and resin typically does not contain said compound that has a constitutional unit derived from polyalkylene glycol, described herein below.

Examples of suitable polymers to, and methods to, prepare the secondary water-absorbing agent, or secondary water-absorbing resin particles thereof, are disclosed in for example U.S. Pat. No. 3,661,875, U.S. Pat. No. 4,076,663, U.S. Pat. No. 4,093,776, U.S. Pat. No. 4,666,983, and U.S. Pat. No. 4,734,478. Most preferred polymers used to make the secondary resin particles and secondary water-absorbing agent herein are polyacrylates/acrylic acids and derivatives thereof, preferably (slightly) network crosslinked polymers partially neutralized polyacrylic acids and/or starch derivatives thereof. Exemplary processes for producing these resins and agents are described in U.S. Pat. No. 4,666,983 (Tsubakimoto et al.), issued May 19, 1987, issued Nov. 25, 1986; U.S. Pat. No. 5,140,076 (Harada); U.S. Pat. No. 6,150,469 (Harada). Crosslinking can be affected during polymerization by incorporation of suitable crosslinking monomers, and/or after polymerization by reaction with a suitable reactive crosslinking agent.

Suitable general methods for carrying out surface crosslinking and crosslinking in general are disclosed in U.S. Pat. No. 4,541,871 (Obayashi), issued Sep. 17, 1985; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; U.S. Pat. No. 5,140,076 (Harada); U.S. Pat. No. 6,150,469 (Harada) and U.S. Pat. No. 4,076,663

The absorbent core comprises preferably very little cellulose fibres, preferably less than 10% by weight of the total of primary and if present secondary water-absorbing agent. Also each layer itself preferably comprises less than 10% by weight (of the total of water-absorbing agent present in said layer) of cellulose fibres. This is referred to herein as "substantially cellulose fibres free". More preferably this level is less than 5% or preferably less than 1%, or for example no cellulose fibres are present at all in said layers comprising water-absorbing agents, or in said absorbent core.

In one embodiment, the storage layer comprises a first and second layer of said secondary water-absorbing material, and a first substrate, e.g. nonwoven, and a second substrate, enclosing said first and second layer of the storage core, whereby preferably said secondary water-absorbing agent is deposited on said first and second substrates and whereby thermoplastic adhesive material covers said secondary water-absorbing agent on the respective first and second substrate, such that each layer comprises said adhesive material and each substrate may be in contact with said adhesive material. Hereby, said first and second layers of the storage layer are preferably combined together such that at least a portion of said thermoplastic adhesive material of said first layer contacts at least a portion of the thermoplastic adhesive material of said second layer. The secondary water-absorbing agent may be distributed homogeneously, or in a pattern (non-homogeneously distributed). Preferred methods and storage layers are described in for example U.S. application Ser. No. 12/141,122.

The acquisition/storage layer may be made in the same manner, e.g. having a first and second layer, each comprising said primary water-absorbing agent, and said adhesive material, described above, and a substrate, as described above.

In one embodiment herein, a suitable storage layer may be produced using the method described in U.S. patent application Ser. No. 10/776,839, whereby a laydown drum is provided with a series of reservoirs for the water-absorbing agent, having a shape and volume substantially defined by the desired shape and volume of said storage layer. The acquisition/storage layer may be made by the same or similar method as described above for the storage layer.

In one embodiment, the acquisition/storage layer comprises a coversheet that covers the water-absorbing agent of said layer, either on the side facing the user (or facing or contacting the topsheet) in use, or on the side facing the storage layer, or on both sides. In one embodiment, the coversheet is folded or wrapped around the water-absorbing agent of to form a preferred acquisition/storage layer for sue herein. The coversheet may be a tissue material, or a woven sheet, or preferably nonwoven sheet, such as carded, spunbond and/or meltblown sheet materials, or laminates thereof, such as a SMS or SMMS or SMMMS material. The coversheet may be hydrophilic. It may be made form a hydrophobic material that is treated with a hydrophilic agent.

In one embodiment, the absorbent article herein comprises a backsheet, a (nonwoven) coversheet for a first side of the storage layer, one or two (nonwoven) coversheet to cover the other side of the storage layer and the first side of the acquisition/storage layer, and a (nonwoven) coversheet to cover the opposite side of the acquisition/storage layer, then optionally an additional acquisition layer and then a topsheet, facing the user in use.

The secondary water-absorbing agent may be present at a higher level by weight than the primary water-absorbing agent. The secondary water-absorbing agent may be present together with the primary water-absorbing agent in the same region or layer, e.g. mixed, or it may be present in a separate region or layer; typically the secondary water-absorbing agent is at least present in said so-called storage layer, described herein. The primary water-absorbing agent described herein is preferably comprised by at least said acquisition/storage layer of the absorbent article, as described herein.

In particularly preferred embodiments, the absorbent core is narrower in crotch region than it is in either, or both, of the waist regions. Preferably, the ratio of the average width of the core at transverse axis of the core, to the largest width of the core (e.g. in either of first waist region or second waist region) is from 70:100 to 95:100, or from 80:100 to 90:100, or from 82:100 to 90:100.

The absorbent core may comprise in addition to the acquisition/storage layer and storage layer, a cellulose containing acquisition layer, such as chemically stiffened, curled and/or twisted cellulose, for example present between the topsheet and the acquisition/storage layer. In that case, aid acquisition layer may then be very thin, e.g. having an average caliper of 1 mm or less. However, in one embodiment, the absorbent article does not comprise any additional cellulose-containing acquisition layer or no acquisition layer at all.

The acquisition/storage layer may be in direct contact with said storage layer, or an intermediate layer may be present, between an acquisition/storage layer and a storage layer, such as a nonwoven storage layer cover material. The acquisition/storage layer and/or storage layer may be covered completely or partially by one or more of such nonwoven cover materials. One preferred cover material comprises a spunbonded, a melt-blown and a further spunbonded layer (i.e., a SMS material). The non-woven materials are suitably made using synthetic fibres, such as polyethylene, polyester and, most preferably, polypropylene. Highly preferred are permanently hydrophilic nonwovens, and in particular nonwovens with durably hydrophilic coatings. Such hydrophilicity may be provided by surfactant treatment of the nonwoven. An alternative material comprises an SMMS-structure, or a SMMMS structure, or optionally a cellulosic tissue structure.

Suitably, the acquisition/storage layer has the same surface area as the storage layer or smaller. Preferably, the acquisition/storage layer is laterally centred on the storage layer with the same lateral width but a shorter longitudinal length than storage system. The acquisition/storage layer may also be narrower than the storage layer while remaining centred thereon. The acquisition/storage layer may suitably have an area ratio with respect to the storage system of 1.0. Preferably, the area ratio is less than 1.0 (e.g., less than about 0.75), more preferably less than about 0.50.

The acquisition/storage layer and/or storage layer may comprise an uneven distribution of the water-absorbing agent(s), based on its basis weight, in one or both of the machine and cross directions.

In one embodiment, the absorbent core, or the acquisition/storage layer and/or the storage layer thereof, is obtained by combining the primary and/or secondary water-absorbing agent with a thermoplastic and/or adhesive material that is fibrous, e.g. which structures or stabilizes the layer or core and thus allows removal of some or all of the cellulose fibres that are often present in the storage layer or core to stabilize or structure the water-absorbing agent(s). The absorbent core, storage layer and/or acquisition/storage layer may be substantially cellulose (fibres) free, as mentioned above and as is for example also described in aforementioned U.S. patent application Ser. No. 10/776,839.

The storage layer may have one or more regions with an average density greater than about 0.2 g/cm$^3$, or preferably at least 0.3 g/cm$^3$, or possibly even greater than 0.4 g/cm$^3$.

Suitably, an acquisition/storage layer, comprising the primary water-absorbing agent herein, may have one or more regions with an average density of 0.2 g/cm$^3$ or more, preferably 0.3 g/cm$^3$ or more, or possibly even 0.4 g/cm$^3$ or more.

The absorbent article herein is preferably very thin, having an absorbent core with a maximum dry caliper in the crotch region of less than about 4.5 mm, preferably less than 4.0 mm, or even preferably less than 3.5 mm, or even less than 3.0 mm. This is measured by dividing the crotch regions in areas of 2 cm×2 cm, and measuring the caliper per region, to obtain a maximum value for the caliper in the crotch region. The absorbent article preferably is also very thin, having preferably a maximum dry caliper of less than about 5.5 mm, preferably less than 5.0 mm, or even preferably less than 4.5 mm, or even less than 4.0, as measured in the crotch region as set out above.

Primary Water-Absorbing Agent

The primary water-absorbing agent of herein is a water-absorbing agent containing primary water-absorbing resin particles obtained by polymerizing an acid group-containing unsaturated monomer, said agent having typically a Centrifuge Retention Capacity (CRC) ranging from 5 to 20 g/g and including a compound that has a constitutional unit derived from polyalkyleneglycol and that is other than the unsaturated monomer (herein also referred to as "compound"); and a polyvalent metal salt.

Said compound and said polyvalent metal salt exist on at least one of the inside, the surface, and vicinity of the surface of the water-absorbing resin particles. It is preferable that said compound and/or said polyvalent metal salt are attached to the water-absorbing resin particles; and/or it is preferable that the compound and/or the polyvalent metal salt are present in a free-state, without forming a chemical bond with the water-absorbing resin particles, and/or that they are separable from the water-absorbing resin particles.

Said compound has a constitutional unit derived from polyalkyleneglycol, provided that this is preferably not an unsaturated monomer, whose weight-average molecular weight is less than 1000, more preferably less than 800.

The primary agent typically comprises said primary water-absorbing resin particles at a level of at least 50 weight % or more with respect to the whole amount of the primary water-absorbing agent, preferably at a level of from 60 to 99.9 weight %, more preferably 70 to 99.9 weight %, further preferably 80 to 99.9 weight %, and further more preferably 90 to 99.9 weight %.

The primary water-absorbing resin is preferably present in particulate form, e.g. as spherical particles; agglomeration of spherical particles; compressed spherical particles; an irregularly pulverized shapes; shapes obtained by granulating the irregularly pulverized shape. The primary water-absorbing resin may also be present as foamed shape with pores.

The water-absorbing resin particles are preferably particles of water-absorbing resin having an internal crosslinked structure obtained by polymerizing an acid group-containing unsaturated monomer. The acid group-containing unsaturated monomer is not particularly limited as long as it is a monomer containing an acid group such as a carboxyl group and a sulfo group. In particular, a carboxyl group-containing monomer is preferable in terms of water-absorption properties.

Examples of water-absorbing resin obtained by polymerizing an acid group-containing unsaturated monomer include: a polymer obtained by polymerizing and crosslinking a carboxyl group-containing unsaturated monomer such as (meta)acrylic acid, maleic anhydride, maleic acid, fumaric acid, crotonic acid, itaconic acid, and cinamic acid and/or salt (neutralized product) thereof; hydrolysate of starch-acrylonitrilegraft polymer; starch-acrylic acid graft polymer; saponified vinyl acetate-acrylic acid ester copolymer; hydrolysate of acrylonitrile copolymer or acrylamide copolymer, or crosslinked product thereof; crosslinked denatured polyvinylalcohol containing a carboxyl group; crosslinked isobutylene-maleic anhydride copolymer; and combination of two or more of them.

Preferable examples of the water-absorbing resin include: partially neutralized crosslinked polyacrylic acid polymer disclosed in U.S. Pat. Nos. 4,625,001, 4,654,039, 5,250,640, and 5,275,773 and European Patent No. 456136 etc.; starch-acrylic acid graft polymer that is crosslinked and partially neutralized, disclosed in U.S. Pat. No. 4,076,663; isobutylene-maleic acid copolymer disclosed in U.S. Pat. No. 4,389,513; saponified vinyl acetate-acrylic acid copolymer disclosed in U.S. Pat. No. 4,124,748; hydrolysate of acrylamide (co)polymer disclosed in U.S. Pat. No. 3,959,569; and hydrolysate of acrylonitrile polymer disclosed in U.S. Pat. No. 3,935,099.

Among them, the water-absorbing resin is more preferably a crosslinked polyacrylic acid (salt) polymer or a similar polymer obtained by polymerizing a monomer including acrylic acid and/or salt (neutralized product) thereof as a main component. The crosslinked polyacrylic acid (salt) polymer or a similar polymer is a polymer with an internal crosslinked structure that is obtained by polymerizing a monomer (except for a crosslinking agent) containing preferably 50 to 100 mol %, more preferably 70 to 100 mol %, and still more preferably 90 to 100 mol % of acrylic acid and/or salt thereof.

Furthermore, it is preferable that 45 to 85 mol % of a carboxyl group included in the crosslinked polyacrylic acid (salt) polymer or a similar polymer is neutralized to form salt. In other words, a rate of neutralization of an acid group included in particles of the water-absorbing resin ranges preferably from 45 to 85 mol %, more preferably from 50 to 85 mol %, still more preferably from 55 to 80 mol %, and particularly preferably from 60 to 75 mol %.

The rate of neutralization of an acid group in the water-absorbing resin particles can be calculated based on (i) an amount of an acid group-containing unsaturated monomer that has not been neutralized and (ii) an amount of all bases used in neutralization before polymerization, during polymerization, and/or after polymerization. Furthermore, the rate of neutralization may be obtained by extracting extractable polymer content from the water-absorbing resin particles and titrating the extractable polymer content.

The primary water-absorbing resins included in the primary water-absorbing agent of the present invention have a cross linked structure at least inside the water-absorbing resin, preferably inside and at a surface of the water-absorbing resin. The internal crosslinked structure may be a self-crosslinked structure without a crosslinking agent or may be a structure that is obtained by copolymerizing or reacting an internal crosslinking agent that includes two or more polymerizable ethylenic double bonds or two or more functional groups in one molecule, such as a hydroxyl group, an amino group, an epoxy group, an oxetane group, an ethyleneimine group (aziridine group), an isocyanate group, oxazoline, cyclocarbonate, oxazolidinone, cyclic urea, azetidinium base, and chlorohydrin. Specific examples of the internal crosslinking agent with two or more polymerizable ethylenic double bonds include N,N'-methylenebis(meth)acrylamide, (poly)ethylene glycol di(meth)acrylate, (poly)propylene glycol di(meth)acrylate, trimethylolpropane tri(meth)acrylate, glycerine tri(meth)acrylate, glycerine acrylate methacrylate, ethylene oxide denatured trimethylolpropane tri(meth)acrylate, pentaerythritol hexa(meth)acrylate, triallyl cyanurate, triallyl isocyanurate, triallyl phosphate, triallyl amine, and poly (meth) allyloxy alkane.

Examples of the internal crosslinking agent with two or more functional groups, i.e., the internal crosslinking agent with two or more covalent-bondable functional groups or ionic-bondable functional groups, include: a polyhydric alcohol compound, such as ethylene glycol, diethylene glycol, propylene glycol, triethylene glycol, tetraethylene glycol, 1,3-propanediol, dipropylene glycol, 2,2,4-trimethyl-1,3-pentanediol, glycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylol propane, diethanolamine, triethanolamine, polyoxypropylene, and oxyetylene-oxypropylene block copolymer; polyhydric alcohol such as polyglycerin and pentaerythritol; sugar alcohol such as erythritol, xylitol, sorbitol, mannitol, maltitol, lactitol, and oligosaccharide alcohol; aldose such as xylose, glucose, gulose, mannose, and idose; ketose such as fructose and sorbose; triethylenetetramine, tetraethylenepentamine, pentaethylenehexamine, 2-amino-2 hydroxymethyl-1,3-propanediol, and N,N-bis(2-hydroxyethyl)ethylenediamine; polyvalent metal compound such as hydroxide and chloride of zinc, calcium, magnesium, aluminum, iron, or zirconium; polyglycidyl ether such as (poly)ethleneglycol diglycidyl ether and glycerol diglycidyl ether; ethylenediamine; alkylenecarbonate such as etylenecarbonate and propylenecarbonate; and gycidyl(meth)acrylate.

It is more preferable that the primary water-absorbing resin used herein is crosslinked by both an internal crosslinking agent with four or more functional groups capable of forming a covalent bond with an acid group and an internal crosslinking agent with two or more polymerizable ethylenic double bonds.

This allows further increasing liquid-permeability of the obtained water-absorbing resin and water-absorbing agent. Here, the internal crosslinking agent with four or more functional groups capable of forming a covalent bond with an acid group is preferably one of the internal crosslinking agents as described above. Among them, it is more preferable that the internal crosslinking agent is one of sugar alcohol. It is still more preferable that the internal crosslinking agent is one of erythritol, xylitol, and sorbitol. They are preferable in terms of very high safety, too.

In case the primary water-absorbing resin herein is crosslinked with an internal crosslinking agent with two or more polymerizable ethylenic double bonds in absence of an internal crosslinking agent with four or more functional groups capable of forming a covalent bond with an acid group it is preferable that the internal crosslinking agent with two or more polymerizable ethylenic double bonds has more than 0.5 w % of the unsaturated monomer, more preferably more than 1 w %, more preferably more than 2 w %, but not more than 15 w %.

It is preferable that the water-absorbing resin is surface crosslinked as well as internally crosslinked. The surface crosslinking of the primary water-absorbing resin is present on a surface layer of the particles (vicinity of surface: vicinity that is several 10 µm or less away from the surface in general) of the water-absorbing resin, so that on said surface an area is formed where the crosslinking density is higher than other internal areas.

Examples of preferred surface crosslinking agents include polyhydric alcohol compound, an epoxy compound, a polyamine compound, a condensate of a polyamine compound with a haloepoxy compound, an oxazoline compound, a monooxazolidinone compound, a dioxazolidinone compound, a polyoxazolidinone compound, an alkylenecarbonate compound etc. Specifically, surface crosslinking agents disclosed in U.S. Pat. No. 6,228,930 specification, U.S. Pat. No. 6,071,976 specification, U.S. Pat. No. 6,254,990 specification etc. may be used. More specifically, examples of the surface crosslinking agents include: polyhydric alcohol compounds, such as ethylene glycol, diethylene glycol, triethylene glycol, tetraethylene glycol, monopropylene glycol, 1,3-propanediol, dipropylene glycol, 2,3,4-trimethyl-1,3-pentanediol, glycerin, polyglycerin, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyamine compounds such as ethylenediamine, diethylenetriamine, triethylenetetramine, tetraethylenepentamine, pentaethylenehexamine, polyethylenimine, and polyamidopolyamine; haloepoxy compounds such as epichlorohydrin, epibromohydrin and α-methylepichlorohydrin; condensates between the above polyamine compounds and the above haloepoxy compounds; oxazolidinone compounds such as 2-oxazolidinone (U.S. Pat. No. 6,559,239); oxetane compounds; cyclic urea compounds; and alkylene carbonate compounds such as ethylene carbonate (U.S. Pat. No. 5,409,771).

The primary water-absorbing agent includes as an essential component a compound that includes a constitutional unit derived from polyalkyleneglycol and that is other than an unsaturated monomer, which is preferably present without forming a chemical bond with the water-absorbing resin or is separable from the water-absorbing resin particles. Further, the compound is present on the inside, the surface, and vicinity of the surface of the water-absorbing resin particles. It is particularly preferable that the compound is included in the surface.

Examples of the compound include polyalkyleneglycol, an ester compound of polyalkyleneglycol, and an ether compound of polyalkyleneglycol.

As for an alkylene unit of polyalkyleneglycol, it is typically a compound of the chemical formula (HO—$((CH_2)_n$-$0)_m$-H), or derivative thereof, whereby n preferably ranges from 1 to 10, more preferably from 2 to 6, still more preferably from 2 to 3, and particularly preferably 2. The compound may be a homopolymer, a block polymer, or a random copolymer. m in the above general formula may be 2 or more, more preferably 5 or more, and still more preferably 10 or more.

An end of the compound may be OH or it may be modified; the compound may thus have no hydroxyl groups, or it may have one or more hydroxyl groups derived from polyalkyleneglycol in its molecular chains. Examples of the compound include: polyalkyleneglycol such as polyethyleneglycol, polypropyleneglycol, polyethyleneglycol-polypropyleneglycol copolymer; polyalkyleneglycolmonoalkylether such as polyethyleneglycolmonoalkylether and polypropyleneglycolmonoalkylether; and polyalkyleneglycol mono fatty acid ester such as polyethyleneglycol mono fatty acid ester and polypropyleneglycol mono fatty acid ester.

It is preferable that the compound does not include a radical polymerizable group, such as ethylene double-bond group such as a vinyl group and an allyl group, to avoid formation of a chemical bond with the water-absorbing resin particles.

In one embodiment herein it is preferred that said compound is present without forming a chemical bond with the water-absorbing resin particles and/or that said compound is separable from the water-absorbing resin particles.

Alternatively, or in addition, it may be preferred that said polyvalent metal salt, described hereinafter, is present without forming a chemical bond with the water-absorbing resin particles and/or that said polyvalent metal salt is separable from the water-absorbing resin particles.

The alkyl group in the polyalkyleneglycolmonoalkylether may be linear, branched, or cyclic alkyl group. Among them, the linear alkyl group is preferable. The number of carbon atoms of the alkyl group is not particularly limited, but preferably ranges from 2 to 3000, and more preferably ranges from 2 to 1000.

Further, a fatty acid in the polyalkyleneglycol mono (or optionally di) fatty acid ester is not particularly limited, but is preferably a saturated fatty acid for the above reason. Further, the number of carbon atoms of the fatty acid is not particularly limited, but preferably ranges from 2 to 3000 and more preferably ranges from 2 to 1000. A hydrocarbon portion of the fatty acid may be linear or branched. More specifically, examples of the fatty acid include ethanoic acid (acetic acid), propanoic acid (propionic acid), butanoic acid (butyric acid), 2-methylpropionic acid (isobutyric acid), pentanoic acid (valeric acid), 3-methylbutanoic acid (isovaleric acid), 2,2-dimethylpropionic acid (pivalic acid), hexanoic acid (caproic acid), heptanoic acid (enanthic acid), octanoic acid (caprylic acid), nonaoic acid (pelargonic acid), decanoic acid (capric acid), dodecanoic acid (lauric acid), hexadecanoic acid (palmitic acid), heptadecanoic acid (margaric acid), octadecanoic acid (stearic acid), nonadecanoic acid (tuberculostearic acid), icosanoic acid (arachidic acid), docosanoic acid (behenic acid), tetradocosanoic acid (lignoceric acid), hexadocosanoic acid (cerotic acid), and octadocosanoic acid (montanic acid, melissic acid).

Furthermore, the weight-average molecular weight of the compound that includes a constitutional unit derived from polyalkyleneglycol and that is other than an unsaturated monomer, used in the present invention, ranges preferably from 500 to 50000, more preferably from 1000 to 50000, still more preferably from 1000 to 20000, and particularly preferably from 1000 to 6000. The weight-average molecular weight of the compound being 500 or more is preferable and being 1000 or more is more preferable since it results in a water-absorbing agent with high Saline Flow Conductivity (SFC). Furthermore, the weight-average molecular weight of the compound being 6000 or less is preferable since it ensures excellent handleability and is advantageous in costs.

The weight level of the compound that includes a constitutional unit derived from polyalkyleneglycol ranges preferably from 0.05 to 5 weight %, by weight of the water-absorbing agent.

It is deemed that at least 50%, preferably 70% or more, or 95% or more, of the compound is present without forming a covalent bond with water-absorbing resin particles in the water-absorbing agent of the present invention.

The quantity of the compound without binding with the water-absorbing resin can be determined by extracting an extractable polymer content from the water-absorbing agent and analyzing the extracted content through gel permeation chromatography (GPC) etc. An example of the method is such that a water-absorbing agent is stirred in pure water for 16 hours or more, the aqueous solution is filtered to obtain an extract solution as a filtrate, and the extract solution is analyzed through gel permeation chromatography etc.

The water-absorbing agent of the present invention includes a polyvalent metal, which is believed to increase the SFC of the water-absorbing agent greatly.

Preferable salts include aluminum chloride, polyaluminum chloride, aluminum sulfate, aluminum nitrate, potassium aluminum bisulfate, sodium aluminum bisulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, zirconium nitrate, zirconium ammonium carbonate, zirconium potassium carbonate, and zirconium sodium carbonate. Preferred is an aluminum salt. More preferably, the polyvalent metal salt include aluminum chloride, polyaluminum chloride, aluminum sulfate, aluminum nitrate, potassium aluminum bisulfate, sodium aluminum bisulfate, potassium alum, ammonium alum, sodium alum, and sodium aluminate.

The polyvalent metal salt is preferably water-soluble polyvalent metal salt with water of crystallization.

Particularly preferred salts are aluminum sulfate, aluminum sulfate 18-hydrate and aluminum sulfate 14-hydrate to 18-hydrate.

The amount of the polyvalent metal salt included in the water-absorbing agent herein is preferably 0.001 to 10 weight % and more preferably 0.01 to 5 weight % on the polyvalent metal salt basis with respect to the water-absorbing agent. The amount is preferably 0.0001 to 2 weight % and more preferably 0.001 to 1 weight % on polyvalent metal basis (cation basis) with respect to the water-absorbing agent.

The primary water-absorbing agent of the present invention has Centrifuge Retention Capacity (CRC) ranging from 5 to 20 g/g, preferably from 10 to 20 g/g, and more preferably from 12 to 18 g/g.

SFC of the primary water-absorbing agent of the present invention is preferably 400 $cm^3 \cdot s \cdot 10^{-7}$/g or more, more preferably 600 $cm^3 \cdot s \cdot 10^{-7}$/g or more, and still more preferably 800 $cm^3 \cdot s \cdot 10^{-7}$/g or more. The upper limit of SFC of the water-absorbing agent is not particularly limited, and it is preferably 4000 cm$^3$·s·10$^{-7}$/g or less and more preferably 3000 cm$^3$·s·10$^{-7}$/g or less.

The solid content of the primary water-absorbing agent of the present invention ranges preferably from 80 to 99.9 weight %, more preferably from 85 to 99 weight %, and still more preferably from 90 to 98 weight %.

The primary resin particles may for example be spherical or oval or fiber-shaped. The particles have a each a particle diameter and they have a weight (mass) average particle diameter (D50) ranges preferably from 100 to 850 µm, more preferably from 200 to 600 µm, still more preferably from 250 to 550 µm, and particularly preferably from 300 to 500 µm. Further, logarithmic standard deviation (σξ) ranges preferably from 0.1 to 0.6, more preferably from 0.2 to 0.5, and still more preferably from 0.25 to 0.4.

It may be preferred that the primary water-absorbing agent preferably includes 90 to 99.99 weight % of particles with 1000 to 45 µm particle diameter, or 90 to 99.99 weight % or 95 to 99.99 weight % of particles with 850 to 106 µm particle diameter.

The method for producing the primary water-absorbing agent of the present invention includes typically the steps of:
(A) producing a crosslinked polymer hydrogel by polymerizing an acid group-containing unsaturated monomer in the presence of an internal crosslinking agent;
(B) obtaining water-absorbing resin particles (not surface-crosslinked) by drying the crosslinked polymer hydrogel obtained in the step (A); and
(C) obtaining surface-crosslinked water-absorbing resin particles by surface crosslinking
the water-absorbing resin particles (not surface-crosslinked) obtained in the step (B), and the method further includes at least the steps of:
adding the compound that includes a constitutional unit derived from polyalkyleneglycol and that is other than an unsaturated monomer to a monomer or the water-absorbing resin particles; and
adding polyvalent metal salt to the water-absorbing resin particles.

The step of adding the compound that includes a constitutional unit derived from polyalkyleneglycol may be performed in step (A), or it may be preferred that said compound is added at the same time with, or after adding a surface crosslinking agent and before heating in the step (C).

The step of adding a polyvalent metal salt is preferably performed in the step (C) or after the step (C).

In a preferable example of the method for producing the primary water-absorbing agent herein, the compound that includes a constitutional unit derived from polyalkyleneglycol is mixed in step A with the monomer aqueous solution at the time of polymerization, before or after or simultaneous with adding a possible polymerization initiator. The compound may be added one or more times.

It is preferable that the acid monomer and said compound herein are "water-soluble" means having a solubility in 100 ml of ion-exchanged water at normal pressure and at 25±2° C. of 1 g or more, preferably 5 g or more, and more preferably 10 g or more.

In the step (A), the acid group-containing unsaturated monomer may be polymerized in the presence of a particular amount of a polymerization inhibitor as well as the internal crosslinking agent. The polymerization inhibitor is preferably methoxyphenols, more preferably p-methoxyphene. A radical polymerization initiator may be used such as persulfate (e.g. potassium persulfate, ammonium persulfate, and sodium persulfate), t-buthylhydroperoxide, hydrogen peroxide, 2,2'-azobis(2-amidinopropane)dihydrochloride, 2-hydroxy-1-phenyl-propane-1-one, and benzoinmethylether may be used.

In the case of using the radical polymerization initiator, a reducing agent for promoting decomposition of the radical polymerization initiator, such as sodium sulfite, sodium hydrogen sulfite, ferrous sulfate, and L-ascorbic acid may be used in combination with the radical polymerization initiator, and the combination of the reducing agent and the radical polymerization initiator may serve as a redox initiator. The amounts of the reducing agent and the radical polymerization initiator in use ranges from generally 0.00001 to 0.2 mol % and further from 0.0001 to 0.1 mol % with respect to the monomer.

Instead of using the polymerization initiator, an active energy ray such as radioactive ray, electron beam, and ultraviolet ray may be irradiated to a reaction system to carry out polymerization.

In general, the crosslinked polymer hydrogel (it may hereinafter be abbreviated as hydrogel in the present specification) produced in the step (A) is crushed into pieces with a size suitable for drying, and then subjected to steps such as drying, pulverization, classification, and surface crosslinking, resulting said water-absorbing agent herein.

Drying may take place during such a process, or it may take place subsequently thereto. The hydrogel may also be crushed during polymerization.

In one method herein, the compound that includes a constitutional unit derived from polyalkyleneglycol may be mixed at a time of crushing the hydrogel.

The condition under which the crosslinked polymer hydrogel is dried is not particularly limited. The crosslinked polymer hydrogel is dried at a range, in general, from 150° C. to 250° C., preferably from 150° C. to 220° C., more preferably from 160° C. to 200° C., and still more preferably from 180° C. to 200° C.

Surface-crosslinked water-absorbing resin particles are preferably obtained by surface crosslinking the, preferably internally cross-linked, water-absorbing resin particles, e.g. by adding 0.001 to 10 parts by weight, more preferably 0.01 to 5 parts by weight, with respect to 100 parts by weight, of the water-absorbing resin particles (water-absorbing resin particles that are not surface-crosslinked), of a surface crosslinking agent, described above.

After mixing with the surface crosslinking agent, the resulting water-absorbing resin particles are preferably subjected to a heat treatment with a heating temperature preferably in the range of 120 to 250° C., more preferably 150 to 250° C.

The step of adding the compound that includes a constitutional unit derived from polyalkyleneglycol may (also) be performed at the same time with, or after addition of the surface crosslinking agent in the step (C) and then preferably before the heat treatment step.

The compound that includes a constitutional unit derived from polyalkyleneglycol may be added directly and purely, or as a solution or as a dispersion, e.g. an aqueous solution or dispersion, preferably an aqueous solution. The concentration of the solution etc. may range substantially from 1 to 50 weight %. If necessary, a surfactant etc. may be added. A solvent is evaporated according to necessity.

The polyvalent metal salt may be added in or after the step (C) preferably before, during or after the surface crosslinking step, and preferably before the heat treatment step.

Test methods used herein:
Solid content:
Solid content indicates a ratio of a component that does not evaporate at 180° C. to the water-absorbing agent. A relation between the solid content and water content is as follows.

Solid content(weight%)=100−water content(weight%)

The solid content was measured as follows.
Approximately 1 g of a water-absorbing agent (weight $W_1$) was put in an aluminum cup (weight $W_0$) with a bottom diameter being approximately 5 cm, and left still in a windless drier at 180° C. for 3 hours so that the water-absorbing agent is dried. The weight of aluminum cup+the water-absorbing agent ($W_2$) after the drying was measured, and the solid content was calculated as follows:

solid content(weight%)=(($W_2−W_0$)/$W_1$)×100

Molecular weight and elution weight of polyethyleneglycol (PEG) having eluted from water-absorbing resin particles and water-absorbing agent:
1000 g of ultra pure water (specific resistance was 1.5MΩ·cm or more) was poured into a covered plastic receptacle of 1 liter in capacity, 1.00 g of water-absorbing resin or a water-absorbing agent was put in the aqueous solution, the resulting solution was stirred by Teflon® stirrer tip (length 35 mm, thickness (diameter of cross section perpendicular to a longitudinal direction) 7 mm, stick-like shape) at 600 rpm for 16 hours, so that water-soluble component of the water-absorbing resin particles or the water-absorbing agent was extracted. The extract solution was filtered by a filter paper (ADVANTEC Toyo Kaisha, Ltd., product name: JIS P 3801, No. 2, thickness 0.26 mm, diameter of captured particles 5 μm) with use of a Buchner funnel to obtain a resultant filtrate, and the whole amount of the resultant filtrate was put in an eggplant-shaped flask with 1 liter in capacity, and water was evaporated at 60° C. by an evaporator (produced by Yamato Scientific Co., Ltd., product name: Rotary Evaporator RE50). Next, 10.0 ml of an eluant as explained below was poured in the eggplant-shaped flask from which water had evaporated, the internal side of the flask was washed well (dried and condensed objects were dissolved), and the resulting solution was filtered by a filter with 0.45 μm (product name: chromato disc, 25A, hydrophilic 0.45 μm, produced by GL Sciences Inc.), so that a GPC (gel permeation chromatography) measurement sample was obtained. The sample was measured under the following GPC measurement conditions, and the molecular weight and the elution weight of PEG having eluted was calculated using a calibration curve as presented below.

GPC measurement conditions:
Eluant: aqueous solution obtained by dissolving $NaH_2PO_4 \cdot 2H_2O$ and $Na_2HPO_4 \cdot 12H_2O$ in ultra pure water so that concentration of $NaH_2PO_4 \cdot 2H_2O$ is 60 mM and concentration of $Na_2HPO_4 \cdot 12H_2O$ is 20 mM.
Standard sample: 0.005 g of Poly(ethylene glycol) Standard purchased from Polymer Standards Service GmbH ((i) Mw=330, (ii) Mw=600, (iii) Mw=1000, (iv) Mw=2000, (v) Mw=6000, (vi) Mw=11000, (vii) Mw=23000) was dissolved in 10.0 ml of eluant and subjected to GPC measurement so as to form a calibration curve.
GPC system: SHODEX GPC-SYSTEM-21
Guard column: SHODEX Asahipak GF-1G7B (produced by Showa Denko K.K.)
Sample column: Two TOSOH GMPWXLs directly connected with each other (produced by Tosoh Corporation)
Column temperature: 35° C. (constant)
Flow rate: 0.5 ml/min
UV detector: wavelength 205 nm Extractable polymer content
Into a covered plastic receptacle of 250 ml in capacity, 184.3 g of saline was weighed out. Then, 1.00 g of water-absorbing agent was added to this aqueous solution, and they were stirred for 16 hours, and thus soluble components were extracted from the resin. The resultant extract liquid was filtrated with a filter paper (produced by ADVANTEC Toyo Co., Ltd., product name: (ITS P 3801, No 0.2), thickness: 0.26 mm, diameter of captured particles: 5 μm), and then 50.0 g of the resultant filtrate was weighed out and used as a measuring solution.
To begin with, only the saline was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).
The same titration procedure was carried out also for the measuring solution, thus obtaining titration amounts ([NaOH] ml and [HCl] ml).
For example, in a case of a water-absorbing agent including acrylic acid and its sodium salt in known amounts, the extractable polymer content of the water-absorbing agent was calculated from the average molecular weight of the monomers and the titration amounts obtained from the above procedures, in accordance with the following equation:

Extractable polymer content(wt%)=0.1×(average molecular weight)×184.3×100×([HCl]−[bHCl])/ 1000/1.0/50.0

In the case of unknown amounts, the average molecular weight of the monomers was calculated from the neutralization ratio, determined by the titration, as follows:

Neutralization ratio(mol%)=[1−([NaOH]−[bNaOH])/ ([HCl]−[bHCl])]×100

Content of polyvalent metal salt included in water-absorbing agent (on polyvalent metal basis (cationic basis):
Into a polypropylene beaker of 260 ml in capacity, 1.0 g of a water-absorbing agent was weighed out, 190.0 g of saline (0.9 wt % NaCl aqueous solution) and 10.0 g of 2N hydrochloric acid were added, and the resulting solution was stirred at a room temperature for 30 minutes. After the stirring, the supernatant fluid was filtered by a chromato disc (GL chromato disc 25A, produced by GL Sciences Inc.), and the resultant filtrate was analyzed with plasma emission spectrometry (produced by HORIBA Ltd., ULTIMA) to obtain concentration of polyvalent metal component.
The calibration curve was made based on saline including polyvalent metal component in a known amount. Based on the obtained concentration of polyvalent metal component, content (on polyvalent metal basis (cation basis)) of polyvalent metal salt included in the water-absorbing agent is represented by the following equation.
Content (on polyvalent metal basis (cation basis)) of polyvalent metal salt included in water-absorbing agent:

(wt%)=(concentration of polyvalent metal component in solution(wt%))×200

Mass average particle diameter (D50) and logarithmic standard deviation (σξ) of particle diameter distribution
To determine this, water-absorbing resin particles or a primary water-absorbing agent are/is sieved by JIS standard sieves with mesh openings being 850 μm, 710 μm, 600 μm, 500 μm, 425 μm, 300 μm, 212 μm, 150 μm, 45 μm etc., and the percentage R of the residues is plotted on a logarithmic probability paper. Thus, the particle diameter corresponding to R=50 mass % is read as mass average particle diameter (D50).

Further, the logarithmic standard deviation (σξ) of the particle diameter distribution is obtained as follows (smaller σξ means narrower particle diameter distribution):

$$\sigma\xi = 0.5 \times \ln(X_2/X_1)$$

(where $X_1$ is particle diameter at a time R=84.1% and $X_2$ is particle diameter at a time R=15.9%)

Classification at a time of measuring mass average particle diameter (D50) and logarithmic standard deviation (σξ) of particle diameter distribution is performed as follows: 10.0 g of water-absorbing resin particles or a primary water-absorbing agent is put in the JIS standard sieves (IIDA TESTING SIEVE: diameter 8 cm) with mesh openings being 850 μm, 710 μm, 600 μm, 500 μm, 425 μm, 300 μm, 212 μm, 150 μm, 45 μm etc., and is classified for 5 minutes by a vibrating classifier (IIDA SIEVE SHAKER, TYPE: ES-65 (rotational frequency: 60 Hz 230 rpm, number of concussion: 60 Hz 130 rpm), SER. No. 0501) under conditions that the temperature is a room temperature (23±2° C.) and humidity is 50RH %.

Centrifuge Retention Capacity (CRC):

The Centrifuge Retention Capacity (CRC) as used herein means the absorption capacity for 0.90 mass % aqueous sodium chloride solution (i.e. physiological saline) with no pressure for 30 minutes. CRC also referred to as absorption capacity without load. This is determined as follows: 0.200 g of water-absorbing resin particles or a water-absorbing agent is evenly put in a bag (60 mm×85 mm) made of unwoven fabric (produced by Nangoku Pulp Kogyo K.K., product name: heatron paper, type: GSP-22) and it is heat-sealed, and then immersed in 0.90 mass % aqueous sodium chloride solution (physiological saline) with an excessive amount (in general about 500 ml) at 23 (±2)° C. The bag was drawn up after 30 minutes, the bag was drained of water by a centrifuge (produced by KOKUSAN Co. Ltd., type: H-122) for 3 minutes with a centrifugal force (250 G) described in Edana ABSORBENCY II 441.1-99, and then the weight W1 (g) of the bag was measured. Furthermore, the same operation was performed without the water-absorbing resin particles or the water-absorbing agent, the weight W0 (g) of the bag at that time was measured, and Centrifuge Retention Capacity (CRC) (g/g) was calculated as follows:

$$CRC(g/g) = (W_1(g) - W_0(g))/(\text{weight}(g)\text{ of water-absorbing resin particles or water-absorbing agent}) - 1$$

Saline Flow Conductivity (SFC) (and SFC Measurement Device):

The Saline Flow Conductivity (SFC) as used herein is determined for a gel layer formed in a water-absorbing agent that has absorbed physiological saline and has been swollen under load was measured.

Darcy's Law and a steady flow method are used for measurement of the Saline Flow Conductivity (SFC) (see "Absorbency", edited by P. K. Chatterjee, Elsevier, 1985, pages 42-43, and Chemical Engineering Vol. II, third edition, J. M. Coulson and J. F. Richardson, Pergamon Press, 1978, pages 125-127 for example).

Figure 1:
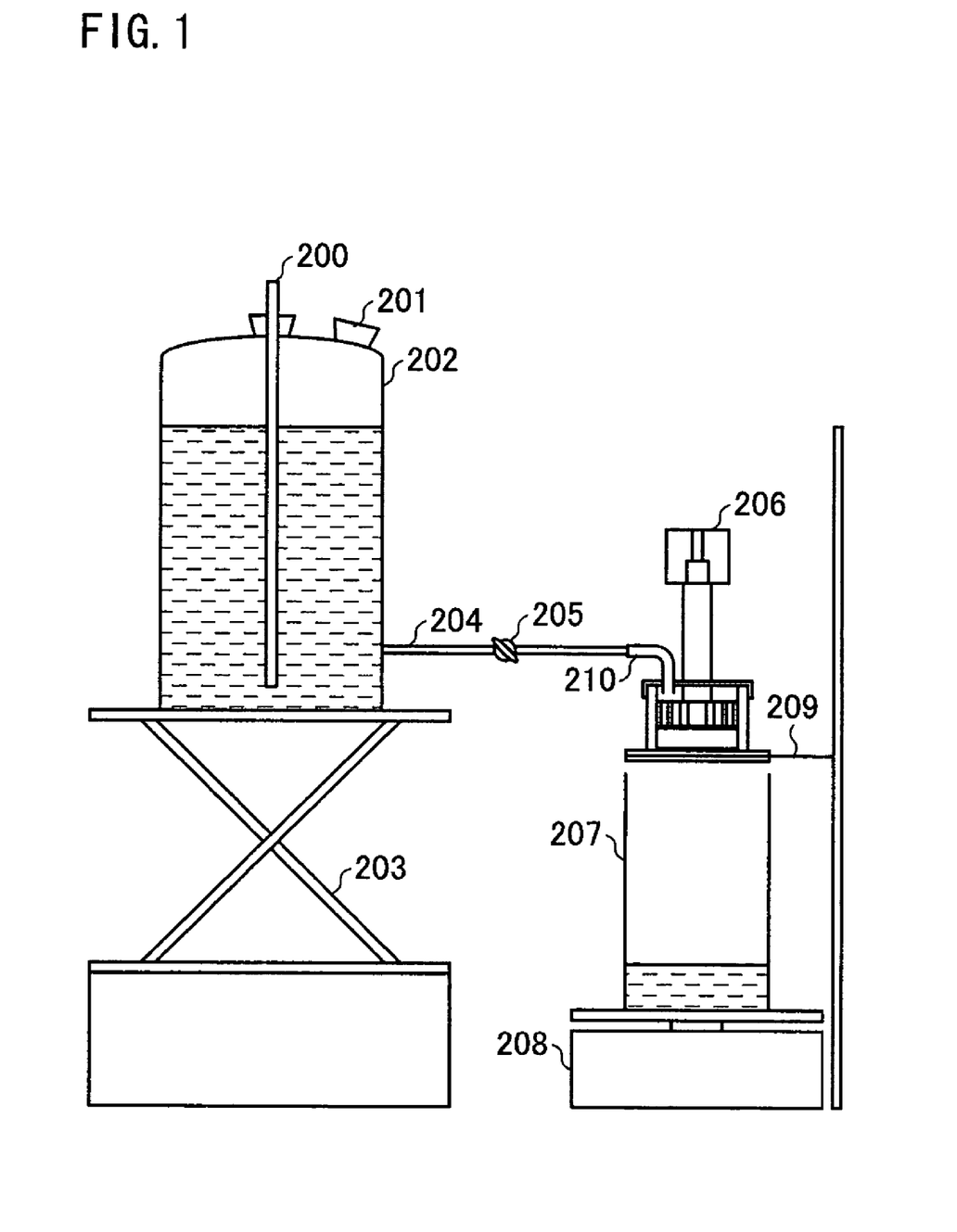
FIG. 1 is a cross sectional view schematically illustrating a measurement device used for measuring the SFC, as used herein.

FIG. 1 illustrates a device suitable for the measurement. The device includes a storage tank (202) with approximately 5 L in capacity, placed on a labo jack (203). The storage tank (202) includes a glass tube with an open end and a rubber plug section (200), each for a function for keeping the height of the still water to be certain. By pulling out a rubber plug section (201), it is possible to add a solution to the storage tank (202). The storage tank (202) has a solution exit provided under a solution surface in the storage tank (202), and a glass tube (204) with a valve (205) is connected with the storage tank (202). Flow of the solution is controlled by opening/closing the valve (205). The glass tube (204) is connected with a flexible tube (210). The other end of the flexible tube (210) is provided so as to flow the solution to an SFC device (206) shown as a whole. The SFC device (206) is provided on a supporter (209) having a stainless wire mesh with a mesh opening of 1 mm. A collection tank (207) for collecting the solution is provided under the supporter (209). The collection tank (207) is provided on a scale (208). The scale (208) is connected with a computer so that the amount of the collected solution is recorded per a certain time.

For convenience of understanding FIG. 1, devices at the right side (such as the SFC device 206, the collection tank 207, the scale 208, and the supporter 209) are illustrated in FIG. 1 in an enlarged size compared with the devices at the left side.

Figure 2:
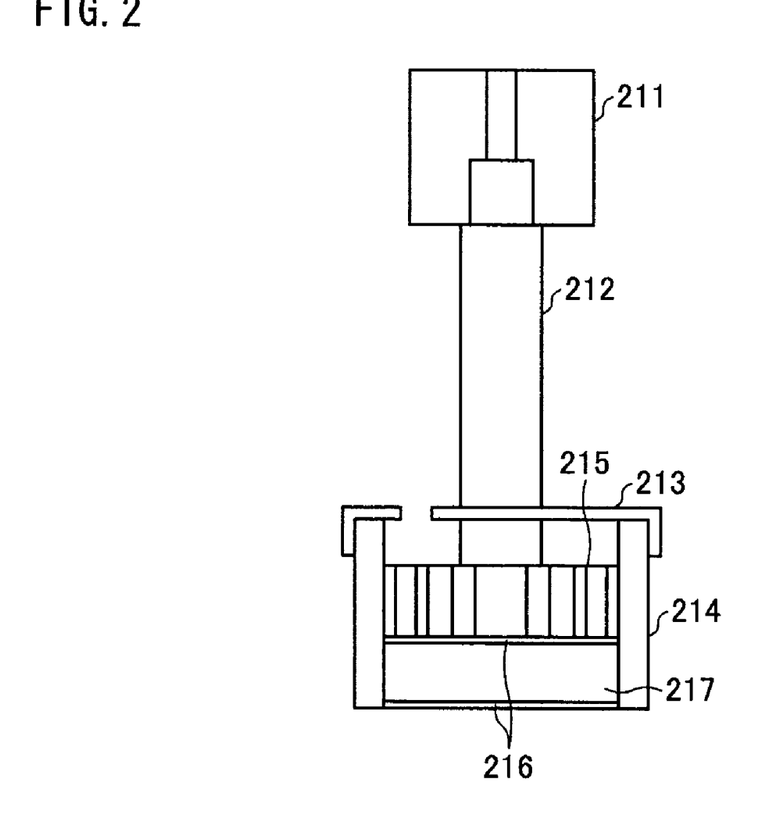
FIG. 2 is a cross sectional view schematically illustrating a part of the measurement device used for measuring said SFC.
Figure 3:
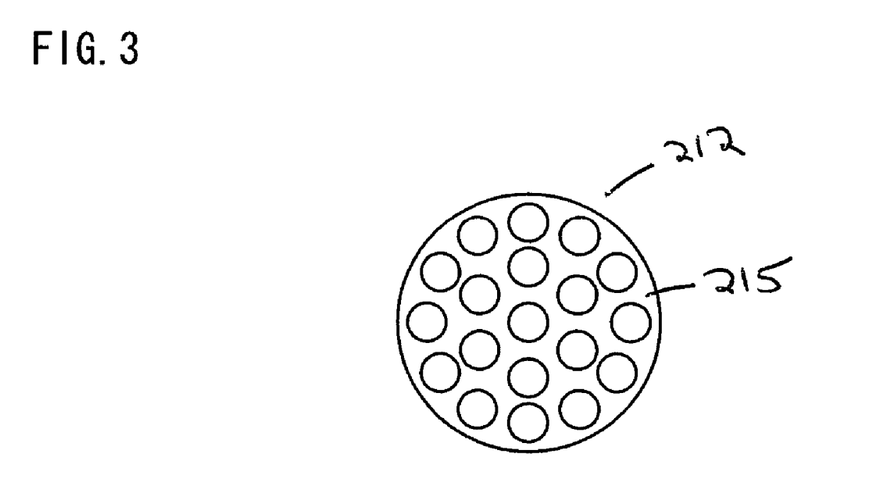
FIG. 3 is a bottom view illustrating a piston head of the measurement device used for measuring said SFC.

As illustrated in FIG. 2, the SFC device basically includes: a cylinder (214) with a stainless wiremesh at its bottom (obtained by modifying LEXANR or similar product); a piston (212) (obtained by modifying LEXANR or similar product); a cover (213) (obtained by modifying LEXANR or similar product) with an orifice to which a tube for flowing the solution is inserted; and a weight (211). As illustrated in FIG. 3, the piston (212) includes a piston head (215) with holes. As illustrated in FIG. 3, each of the holes of the piston head (215) has a cylindrical structure that penetrates the piston head (215) in a vertical direction. A wiremesh (216) with 400 meshes (mesh opening: 38 μm) (produced by Weisse & Eschrich, material: SUS304, mesh width: 0.038 mm, wire diameter: 0.025 mm) is attached to a lower surface of the piston head (215). The piston head (215) has a diameter a little smaller than the internal diameter of the cylinder (214) and has a size that allows the piston head (215) to move sliding inside the cylinder (214) in a vertical direction without any disturbance. An upper part of the shaft of the piston (212) is fabricated so that the weight can be placed on the upper part. The cylinder (214) has an internal diameter of 6.00 cm (bottom area: 28.27 cm² 28.27 cm2), a wall thickness of 0.5 cm; and a height of 6.0 cm. A wiremesh (216) with 400 meshes (mesh opening: 38 μm) (produced by Weisse & Eschrich, material: SUS304, mesh width: 0.038 mm, wire diameter: 0.025 mm) is attached to a bottom of the cylinder (214). The cover (213) has a hole a little wider than an outline of the shaft, and has a size that allows the piston (212) to move sliding in the shaft in a vertical direction without any disturbance. Furthermore, the cover (213) has an orifice to which the tube for flowing the solution is inserted. The weight consisting of the weights of the weight (211) and the piston (212) is adjusted to be 2.07 kPa (0.3 psi) with respect to the bottom surface of the cylinder.

SFC Measurement Method:

First, the height ($h_0$: unit is mm and effective digits are four) and the weight ($W_0$: unit is g and effective digits are four) of the SFC device consisting of the cylinder (214) before a water-absorbing agent being put therein, i.e. in a hollow state; the piston (212); the cover (213); and the weight (211) are measured. Next, 3.00±0.05 g of a water-absorbing agent is weighed out (W: unit is g and effective digits are four). It is preferable that the amount of the weighed water-absorbing agent is adjusted so that d final as explained later ranges from 10 mm to 20 mm and it is more preferable that the amount is adjusted so that d final ranges from 15 mm to 20 mm. For example, in a case where absorption capacity without load (CRC) ranges from 5 g/g to 16 g/g, the amount of the water-absorbing agent is 3.00±0.05 g, in a case where CRC is more than 16 g/g and not more than 20 g/g, the amount of the water-absorbing agent is 2.00±0.03 g, and in a case where CRC is more than 20 g/g and not more than 25 g/g, the amount of the water-absorbing agent is 1.60±0.03 g, and in a case where CRC is more than 25 g/g and not more than 30 g/g, the amount of the water-absorbing agent is 1.30±0.03 g. It is preferable that the amount of the water-absorbing agent to be weighed out is adjusted so that d final as explained later is in the above range. The weighed water-absorbing agent is put on the whole bottom surface of the cylinder (214) so as to be dispersed carefully and evenly. Then, the piston (212), the cover (213), and the weight (211) are provided and the height ($h_1$: unit is mm) of the SFC device is measured. Next, saline (0.9 mass % sodium chloride aqueous solution) is poured in a petri dish with 16 cm or more in diameter and 4 cm or more in height so that the SFC device is immersed in the saline from the bottom up to at least 3 cm. A filter paper (produced by ADVANTEC: No. 2) with 90 mm in diameter was placed on an internal bottom surface of the petri dish. The SFC device in which the water-absorbing agent is put is placed on the filter paper and the water-absorbing agent is caused to be swollen for 60 minutes. After 60 minutes, the SFC device is taken out of the petri dish, and the height ($h_2$: unit was mm and effective digits were four) and the weight ($W_2$: unit was g and effective digits were four) of the SFC device after the water-absorbing agent has been allowed to swell is measured. Thereafter, the SFC device is moved to and put on the supporter (209) of an SFC measurement device, and the flexible tube (210) is provided at the orifice. Next, the valve (205) is opened so as to allow flow of the solution. After starting the flow of the solution and before the amount of the solution that flowed through the gel layer and is collected reached approximately 200 g (as displayed by the scale), an adjustment is made so that the height of still water in the cylinder so that this is kept at 5 cm. This adjustment may be performed by adjusting the height of the labo jack (203) or by adjusting the height of the lower part of the glass tube inserted from the upper part of the storage tank 202. At a time when the height of the still water in the cylinder is adjusted to keep being 5 cm, the computer connected with the scale starts acquiring data indicative of the weight of the solution having been through the gel layer and been collected. Acquisition of the data is performed per 5 sec and until 180 sec. However, when the amount of collected solution reached 2 kg or more after starting the acquisition of the data and before 180 sec, the acquisition of the data is stopped at the time (for example, at 120 sec). On the other hand, when the amount of the collected solution reached 100 g or less at 180 sec after starting the acquisition of the data, the acquisition of the data is prolonged to 600 sec. After ending the acquisition of the data, the valve (205) is closed promptly. After closing the valve (205), the height ($h_3$: unit was mm and effective digits were four) of the SFC device is measured at a time when the solution that poured from the lower part of the cylinder (214) of the SFC device substantially stopped (at a time when the height of the still water surface in the cylinder (214) corresponded to the height of the gel layer). Thereafter, the SFC device is moved onto a cylindrical device with the same internal diameter as that of the cylinder (214), and drip-off is made for 30 minutes. The SFC device was put onto the cylindrical device so that drip-off is properly carried out while the surface right under the wiremesh, on which the water-absorbing agent is provided in the cylinder, dues not touch anything. After the drip-off for 30 minutes, the height ($h_4$: unit in mm) and the weight ($W_4$: unit in g) of the SFC device are measured.

Calculation of SFC:

Time t (sec) acquired by the computer and weight (g) of the collected solution are plotted on a graph as an X-axis and a Y-axis, respectively. The plot is subjected to linear approximation by a least square method, and an inclination (rate: unit g/s) of the line is obtained.

The SFC as used herein is obtained through the following equation:

$$SFC(cm^3 \cdot s \cdot 10^{-7}/g) = (d\text{final} \times \text{rate})/(\text{Area} \times \text{Density} \times \text{Pressure}) \times 10000000$$

where Area ($cm^2$)=28.27, Density ($g/cm^3$)=1.005 (density of saline at 20° C. is used), d final (cm)={$(h_2-h_0)+(h_3-h_0)$}/2/10

Methods to determine the following parameters are described in co-pending applications EP1928511 and US2007/0202772:

Bulk density; Basis Weight; Calliper; Density of a region of the absorbent core or layer thereof.

Example 1

In a polypropylene receptacle of 1 liter in capacity, a solution (A) was prepared by mixing 373.14 g of acrylic acid, 1.49 g of polyethylene glycol diacrylate (molecular weight 523), and 2.25 g of 1.0 weight % diethylenetriamine 5 acetic acid 3 sodium aqueous solution. Furthermore, a solution (B) was prepared by mixing 288.27 g of 48.5 weight % sodium hydroxide aqueous solution and 314.66 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution. 4.50 g of polyethylene glycol 6000 (average molecular weight 6000, produced by KANTO CHEMICAL CO., INC.) and 1.89 g of D-sorbitol were added to the monomer aqueous solution (C) while stirring the monomer aqueous solution (C), thus a monomer aqueous solution (D) was obtained.

Subsequently, at a time when the temperature of the monomer aqueous solution (D) dropped to 97° C., 13.81 g of 3 weight % sodium persulfate aqueous solution was added to the monomer aqueous solution (D) while stirring the monomer aqueous solution (D), and the resulting solution was poured, in an open system, into a stainless bat-shaped receptacle with Teflon® coated inside, that was heated by a hot plate (NEO HOTPLATE H1-1000, produced by IUCHI SEIEIDO CO., LTD.) to have a surface temperature of 100° C. The stainless bat-shaped receptacle has a shape such that the area of the bottom surface is 250×250 mm, the area of the upper surface is 640×640 mm, the height is 50 mm, the central cross section is a trapezoid, and the upper surface is open.

Polymerization started soon after the polymer aqueous solution (D) to which the sodium persulfate aqueous solution had been added was poured into the stainless bat-shaped receptacle. The polymerization proceeded with production of vapor and expansion and effervescence both in vertical and lateral directions, and then the resulting crosslinked polymer hydrogel (hydrogel) contracted to a size a little larger than the bottom surface. The expansion and the contraction ended within approximately 1 minute. The resulting crosslinked polymer hydrogel (hydrogel) was kept in the polymerization receptacle (stainless bat-shaped receptacle) for 3 minutes, and then the crosslinked polymer hydrogel (hydrogel) was taken out. These procedures were carried out in a system open to the air.

The resulting crosslinked polymer hydrogel (hydrogel) was crushed by a meat chopper (MEAT-CHOPPER TYPE: 12VR-400KSOX, produced by Iizuka Kogyo Co., Ltd., die pore diameter: 6.4 mm, number of pores: 38, die thickness: 8 mm) and thus the crosslinked polymer hydrogel was crushed into pieces (crushed particles were obtained). At that time, the crosslinked polymer hydrogel was put in an amount of approximately 350 g/min, and crushing was carried out while deionized water was added in an amount of approximately 80 g/min concurrently with the putting of the crosslinked polymer hydrogel.

The crosslinked polymer hydrogel (crushed into pieces-crushed particles) was spread over a stainless mesh with mesh opening of 850 μm, and was dried with heated wind at 180° C. for 30 minutes. The resulting dried particles were pulverized by a roll mill (WML type roll pulverizer, produced by Inoguchi Giken, Ltd.) and classified by a JIS standard sieve with mesh openings of 850 μm and 45 μm, so that an (irregularly pulverized) primary water-absorbing resin particles, with a solid content of 95 weight %, a mass average particle diameter (D50) of 461 μm, and logarithmic standard deviation (σξ) of particle diameter distribution of 0.34, was obtained.

A surface crosslinking agent made by mixing 0.48 parts by mass of 1,4 butanediol, 0.75 parts by mass of propylene glycol, and 4.0 parts by mass of deionized water was evenly sprayed to and mixed with 100 parts by mass of the resulting water-absorbing resin particles while stirring the 100 parts by mass of the resulting water-absorbing resin particles. The water-absorbing resin particles with which the surface crosslinking agent solution had been mixed were subjected to a heating treatment by a hot drier (temperature: 180° C.) for 75 minutes and surface crosslinking was carried out. After the heating treatment, the resulting water-absorbing resin particles were crushed so that the particles passed a JIS standard sieve with mesh opening of 850 μm. Thus, surface-crosslinked water-absorbing resin particles were obtained.

A mixture solution made by mixing 0.80 parts by mass of aluminum sulfate 27 weight % aqueous solution (8 weight % on aluminum oxide basis), 0.134 parts by mass of sodium lactate 60 weight % aqueous solution, and 0.016 parts by mass of propyleneglycol was added to 100 parts by mass of the surface-crosslinked water-absorbing resin particles. After the addition, the resultant was dried at 60° C. for 1 hour without wind, and the resulting particles were caused to pass the JIS standard sieve with mesh opening of 850 μm, so that a primary water-absorbing agent (1) was obtained. Table 1 shows properties of the primary water-absorbing agent (1). Particle diameter distribution of the water-absorbing agent is substantially the same as that of the water-absorbing resin particles.

Example 2

In a reactor made by attaching a lid to a jacketed stainless-steel twin-arm kneader of 10 liters in capacity equipped with two sigma type blades, 578.1 g of acrylic acid, 4235.0 g of 37 weight % acrylic acid sodium aqueous solution, 605.0 g of deionized water, 7.10 g of polyethylene glycol diacrylate (molecular weight 523), 8.99 g of D-sorbitol (produced by Wako Pure Chemical Industries, Ltd.), and 21.45 g of polyethylene glycol 6000 (average molecular weight 6000, produced by KANTO CHEMICAL CO., INC.) were dissolved, so that a reaction solution was obtained.

Subsequently, the reaction solution was deaerated in nitrogen gas atmosphere for 20 minutes while being adjusted to have a temperature of 25° C. Then, 19.7 g of 15 weight % sodium persulfate aqueous solution and 24.7 g of 0.1 weight % L-ascorbic acid aqueous solution were added to the reaction solution while stirring the reaction solution, and after 30 seconds polymerization started. The temperature at which the polymerization started was 25.2° C.

While crushing a resulting gel, polymerization was carried out at 25 to 95° C., and at 30 minutes after the polymerization had started, a crosslinked polymer hydrogel was taken out. The crosslinked polymer hydrogel had a particle diameter of approximately 10 mm or less.

The crosslinked polymer hydrogel (crushed into pieces) was spread over a stainless mesh with mesh opening of 850 μm, and was dried with heated wind at 180° C. for 45 minutes. The resulting dried particles were further pulverized by a roll mill (WML type roll pulverizer, produced by Inoguchi Giken, Ltd.) and classified by a JIS standard sieve with mesh openings of 850 μm and 45 μm, so that irregularly pulverized water-absorbing resin particles with solid content being 95 mass %, mass average particle diameter (D50) being 465 μm, and logarithmic standard deviation (σξ) of particle diameter distribution being 0.34 was obtained.

A surface crosslinking agent made by mixing 0.48 parts by mass of 1,4 butanediol, 0.75 parts by mass of propylene glycol, and 4.0 parts by mass of deionized water was evenly sprayed to and mixed with 100 parts by mass of the resulting water-absorbing resin particles while stirring the 100 parts by mass of the resulting water-absorbing resin particles. The water-absorbing resin particles with which the surface crosslinking agent solution had been mixed were subjected to a heating treatment by a hot drier (temperature: 180° C.) for 1 hour and surface crosslinking was carried out. After the heating treatment, the resulting water-absorbing resin particles were crushed so that the particles passed a JIS standard sieve with mesh opening of 850 μm. Thus, surface-crosslinked water-absorbing resin particles were obtained.

A mixture solution made by mixing 0.80 parts by mass of aluminum sulfate 27 weight % aqueous solution (8 weight % on aluminum oxide basis), 0.134 parts by mass of sodium lactate 60 mass % aqueous solution, and 0.016 parts by mass of propyleneglycol was added to 100 parts by mass of the surface-crosslinked water-absorbing resin particles. After the addition, the resultant was dried at 60° C. for 1 hour without wind, and the resulting particles were caused to pass the JIS standard sieve with mesh opening of 850 μm, so that a primary water-absorbing agent (2) was obtained. Table 1 shows properties of the primary water-absorbing agent (2). Particle diameter distribution of the water-absorbing agent was substantially the same as that of the water-absorbing resin particles.

Furthermore, measurement of molecular weight and elution weight of polyethyleneglycol having eluted from the primary water-absorbing agent (2) shows that the molecular weight of eluted polyethyleneglycol was the same as the used polyethyleneglycol 6000 and the elution weight of the polyethyleneglycol occupied much of the used polyethyleneglycol 6000 (90% or more of the used polyethyleneglycol 6000).

Example 3

A primary water-absorbing agent (3) was obtained in the same way as Example 1 except that the amount of deionized water in the solution (B) was 318.71 g, the amount of polyethylene glycol 6000 (average molecular weight 6000, produced by KANTO CHEMICAL CO., INC.) added to the monomer aqueous solution (C) was 0.45 g, and the time for the heating treatment for surface crosslinking water-absorbing resin particles was 1 hour. Table 1 shows properties of the primary water-absorbing agent (3).

Example 4

100 parts by mass of the surface-crosslinked water-absorbing resin particles obtained in Example 3 were heated to have a temperature of 150° C., and 1.6 parts by mass of potassium alum (potassium aluminum sulfate 12 hydrate) was evenly mixed with the surface-crosslinked water-absorbing resin particles for 5 minutes while stirring the water-absorbing resin particles, so that a primary water-absorbing agent (4) was obtained. Table 1 shows properties of the water-absorbing agent (4).

Example 5

A primary water-absorbing agent (5) was obtained in the same way as Example 1 except that the amount of deionized water in the solution (B) was 301.11 g, the amount of polyethylene glycol 6000 (average molecular weight 6000, produced by KANTO CHEMICAL CO., INC.) added to the monomer aqueous solution (C) was 18.00 g, and the time for the heating treatment for surface crosslinking water-absorbing resin particles was 75 minutes. Table 1 shows properties of the primary water-absorbing agent (5).

Example 6

A primary water-absorbing agent (6) was obtained in the same way as Example 1 except that the amount of deionized water in the solution (B) was 316.91 g, polyethylene glycol 6000 (average molecular weight 6000, produced by KANTO CHEMICAL CO., INC.) added to the monomer aqueous solution (C) was replaced with 2.25 g of polyethyleneglycol 1000 (average molecular weight 1000, produced by Wako Pure Chemical Industries, Ltd.), and the time for the heating treatment for surface crosslinking water-absorbing resin particles was 1 hour. Table 1 shows properties of the primary water-absorbing agent (6).

Example 7

In a polypropylene receptacle of 1 litter in capacity, a solution (A) was prepared by mixing 373.14 g of acrylic acid, 1.49 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 weight % sodium hydroxide aqueous solution and 319.16 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 101° C. due to heat of neutralization and heat of dissolution. 1.89 g of D-sorbitol was added to the monomer aqueous solution (C) while stirring the monomer aqueous solution (C), thus a monomer aqueous solution (D) was obtained.

Subsequently, polymerization, drying, pulverization, and classification were carried out in the same way as Example 1, so that irregularly pulverized water-absorbing resin particles with solid content being 96 weight %, mass average particle diameter (D50) being 465 μm, and logarithmic standard deviation (σξ) of particle diameter distribution being 0.36 was obtained.

A surface crosslinking agent solution made by mixing 0.48 parts by mass of 1,4 butanediol, 0.75 parts by mass of propylene glycol, 3.4 parts by mass of deionized water, 0.5 parts by mass of polyethylene glycol 6000 (average molecular weight 6000, produced by KANTO Chemical Co., Inc.), and 0.80 parts by mass of aluminum sulfate 27 weight % aqueous solution (8 weight % on aluminum oxide basis), and the mixture solution was evenly sprayed to and mixed with 100 parts by mass of the water-absorbing resin particles while stirring the 100 parts by mass of the water-absorbing resin particles. The water-absorbing resin particles with which the surface crosslinking agent solution had been mixed were subjected to a heating treatment by a hot drier (temperature: 180° C.) for 1 hour and surface crosslinking was carried out.

After the heating treatment, the resulting water-absorbing resin particles were crushed so that the particles passed the JIS standard sieve with mesh opening of 850 μm, thus a primary, surface-crosslinked, water-absorbing agent (7) was obtained. Table 1 shows properties of the primary water-absorbing agent (7).

Comparative Example 1

In a polypropylene receptacle of 1 litter in capacity, a solution (A) was prepared by mixing 373.14 g of acrylic acid, 8.11 g of polyethylene glycol diacrylate (molecular weight 523), and 2.25 g of 1.0 weight % diethylenetriamine 5 acetic acid 3 sodium aqueous solution. Furthermore, a solution (B) was prepared by mixing 288.27 g of 48.5 weight % sodium hydroxide aqueous solution and 309.92 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution.

Subsequently, at a time when the temperature of the monomer aqueous solution (C) dropped to 97° C., 13.81 g of 3 weight % sodium persulfate aqueous solution was added to the monomer aqueous solution (C) while stirring the monomer aqueous solution (C), and the resulting solution was poured, in an open system, into a stainless bat-shaped receptacle with Teflon® coated inside, that was heated by a hot plate (NEO HOTPLATE H1-1000, produced by IUCHI SEIEIDO CO., LTD.) to have a surface temperature of 100° C. The stainless bat-shaped receptacle has a shape such that the area of the bottom surface is 250×250 mm, the area of the upper surface is 640×640 mm, the height is 50 mm, the central cross section is a trapezoid, and the upper surface is open.

Polymerization started soon after the monomer aqueous solution (C) to which the sodium persulfate aqueous solution had been added was poured into the stainless bat-shaped receptacle. The polymerization proceeded with production of vapor and expansion and effervescence both in vertical and lateral directions, and then the resulting crosslinked polymer hydrogel (hydrogel) contracted to a size a little larger than the bottom surface. The expansion and the contraction ended within approximately 1 minute. The resulting crosslinked polymer hydrogel (hydrogel) was kept in the polymerization receptacle (stainless bat-shaped receptacle) for 3 minutes, and then the crosslinked polymer hydrogel (hydrogel) was taken out. These procedures were carried out in a system open to the air.

The resulting crosslinked polymer hydrogel (hydrogel) was crushed by a meat chopper (MEAT-CHOPPER TYPE: 12VR-400KSOX, produced by Iizuka Kogyo Co., Ltd., die pore diameter: 6.4 mm, number of pores: 38, die thickness: 8 mm) and thus the crosslinked polymer hydrogel was crushed into pieces (crushed particles were obtained).

The crosslinked polymer hydrogel crushed into pieces (crushed particles) was spread over a stainless mesh with mesh opening of 850 μm, and was dried with heated wind at 180° C. for 30 minutes. The resulting dried particles were pulverized by a roll mill (WML type roll pulverizer, produced by Inoguchi Giken, Ltd.) and classified by a JIS standard sieve with mesh openings of 850 μm and 45 μm, so that irregularly pulverized water-absorbing resin particles with solid content being 96 weight %, mass average particle diameter (D50) being 463 μm, and logarithmic standard deviation (σξ) of particle diameter distribution being 0.35 was obtained.

A surface crosslinking agent solution made by mixing 0.48 parts by mass of 1,4 butanediol, 0.75 parts by mass of propylene glycol, and 4.0 parts by mass of deionized water was evenly sprayed to and mixed with 100 parts by mass of the resulting water-absorbing resin particles while stirring the 100 parts by mass of the resulting water-absorbing resin particles. The water-absorbing resin particles with which the surface crosslinking agent solution had been mixed were subjected to a heating treatment by a hot drier (temperature: 180° C.) for 1 hour and surface crosslinking was carried out. After the heating treatment, the resulting water-absorbing resin particles were crushed so that the particles passed a JIS standard sieve with mesh opening of 850 μm. Thus, the surface-crosslinked water-absorbing resin particles were obtained. These water-absorbing resin particles were regarded as a comparative water-absorbing agent (1). Table 1 shows properties of the comparative water-absorbing agent (1).

Comparative Example 2

A mixture solution made by mixing 0.80 parts by mass of aluminum sulfate 27 weight % aqueous solution (8 weight % on aluminum oxide basis), 0.134 parts by mass of sodium lactate 60 weight % aqueous solution, and 0.016 parts by mass of propylene glycol was added to 100 parts by mass of the comparative water-absorbing agent (1). After the addition, the resultant was dried at 60° C. for 1 hour without any wind, and the resulting particles were caused to pass a JIS standard sieve with mesh opening of 850 μm, so that a comparative water-absorbing agent (2) was obtained. Table 1 shows properties of the comparative water-absorbing agent (2).

Comparative Example 3

In a reactor made by attaching a lid to a jacketed stainless-steel twin-arm kneader of 10 liters in capacity equipped with two sigma type blades, 578.1 g of acrylic acid, 4235.0 g of 37 weight % acrylic acid sodium aqueous solution, 626.4 g of deionized water, 7.10 g of polyethylene glycol diacrylate (molecular weight 523), and 8.99 g of D-sorbitol (produced by Wako Pure Chemical Industries, Ltd.), were dissolved, so that a reaction solution was obtained.

Subsequently, polymerization, drying, pulverization, and classification were carried out in the same way as Example 2, so that irregularly pulverized water-absorbing resin particles with solid content being 93 weight %, mass average particle diameter (D50) being 460 μm, and logarithmic standard deviation (σξ) of particle diameter distribution being 0.36 was obtained.

A surface crosslinking agent solution made by mixing 0.48 parts by mass of 1,4 butanediol, 0.75 parts by mass of propylene glycol, and 4.0 parts by mass of deionized water was evenly sprayed to and mixed with 100 parts by mass of the resulting water-absorbing resin particles while stirring the 100 parts by mass of the resulting water-absorbing resin particles. The water-absorbing resin particles with which the surface crosslinking agent solution was mixed were subjected to a heating treatment by a hot drier (temperature: 180° C.) for 1 hour and surface crosslinking was carried out. After the heating treatment, the resulting water-absorbing resin particles were crushed so that the particles passed a JIS standard sieve with mesh opening of 850 μm. Thus, surface-crosslinked water-absorbing resin particles were obtained. The water-absorbing resin particles thus obtained were regarded as a comparative water-absorbing agent (3). Table 1 shows properties of the comparative water-absorbing agent (3).

Comparative Example 4

A mixture solution made by mixing 0.80 parts by mass of aluminum sulfate 27 weight % aqueous solution (8 weight % on aluminum oxide basis), 0.134 parts by mass of sodium lactate 60 mass % aqueous solution, and 0.016 parts by mass of propyleneglycol was added to 100 parts by mass of the comparative water-absorbing agent (3). After the addition, the resultant was dried at 60° C. for 1 hour without wind, and the resulting particles were caused to pass the JIS standard sieve with mesh opening of 850 μm, so that a comparative water-absorbing agent (4) was obtained. Table 1 shows properties of the comparative water-absorbing agent (4).

Comparative Example 5

The surface-crosslinked water-absorbing resin particles obtained in Example 1 (to which the mixture solution made of the aluminum sulfate aqueous solution, the sodium lactate aqueous solution, and the propylene glycol was not added) was regarded as a comparative water-absorbing agent (5). Table 1 shows properties of the comparative water-absorbing agent (5).

TABLE 1

| example no. | primary water-absorbing agent no. | compound including constitutional unit derived from polyalkylene glycol | amount of added compound including constitutional structure derived from polyalkyleneglycol | addition of polyvalent metal salt | CRC | SFC |
|---|---|---|---|---|---|---|
| 1 | (1) | PEG6,000 | 1 wt % (added in polymerization) | added | 13.7 | 1102 |

TABLE 1-continued

| | | compound including constitutional unit derived from polyalkylene glycol | amount of added compound including constitutional structure derived from polyalkyleneglycol | addition of polyvalent metal salt | CRC | SFC |
|---|---|---|---|---|---|---|
| 2 | (2) | PEG6,000 | 1 wt % (added in polymerization) | added | 16.2 | 824 |
| 3 | (3) | PEG6,000 | wt % (added in polymerization) | added | 15.2 | 895 |
| 4 | (4) | PEG6,000 | wt % (added in polymerization) | added | 15.4 | 910 |
| 5 | (5) | PEG6,000 | 4 wt % (added in polymerization) | added | 13.1 | 1205 |
| 6 | (6) | PEG1,000 | 0.5 wt % (added in polymerization) | added | 16.5 | 783 |
| 7 | (7) | PEG6,000 | 0.5 wt % (added in surface treatment) | added (in surface Treatment agent) | 14.8 | 945 |
| Comparative example no. | Comparative water-absorbing agent | | | | | |
| 1 | (1) | without PEG | | not added | 16.1 | 331 |
| 2 | (2) | without PEG | | added | 15.6 | 598 |
| 3 | (3) | without PEG | | not added | 16.3 | 344 |
| 4 | (4) | without PEG | | added | 15.9 | 619 |
| 5 | (5) | PEG6,000 | wt % (added in polymerization) | not added | 18.8 | 226 |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

The invention claimed is:

1. An absorbent article comprising an absorbent core, the absorbent core comprising a primary water-absorbing agent; wherein the primary water-absorbing agent comprises (i) water-absorbing resin particles obtained by polymerizing an acid group-containing unsaturated monomer; (ii) a compound that includes a constitutional unit derived from polyalkyleneglycol, that is different from the unsaturated monomer; and (iii) a polyvalent metal salt; wherein the primary water-absorbing agent exhibits a Centrifuge Retention Capacity of from about 5 to about 20 g/g; and wherein the compound is present without forming a chemical bond with the water-absorbing particles and/or the compound is separable from the water-absorbing particles.

2. The absorbent article according to claim 1, wherein the primary water-absorbing agent exhibits a Saline Flow Conductivity of at least about 400 $cm^3 \cdot s \cdot 10^{-7}/g$.

3. The absorbent article according to claim 1, wherein the compound that includes a constitutional unit derived from polyalkyleneglycol does not include a radical polymerizable group.

4. The absorbent article according to claim 1, wherein the compound that includes a constitutional unit derived from polyalkyleneglycol has a weight average molecular weight of from about 500 to about 50,000.

5. The absorbent article according to claim 1, wherein the primary water-absorbing agent is crosslinked by both an internal crosslinking agent with four or more functional groups capable of forming a covalent bond with an acid group and an internal crosslinking agent with two or more polymerizable ethylenic double bonds.

6. The absorbent article according to claim 1, wherein the primary water-absorbing agent is crosslinked by an internal crosslinking agent with two or more polymerizable ethylenic double bonds, in the absence of an internal crosslinking agent with four or more functional groups capable of forming a covalent bond with an acid group, the internal crosslinker being used at a level of more than about 2% by weight of the unsaturated monomer.

7. The absorbent article according to claim 1, wherein the absorbent core further comprises a secondary water-absorbing agent, wherein the secondary water absorbing agent exhibits a Centrifuge Retention Capacity of at least about 25 g/g.

8. The absorbent article according to claim 7, wherein the absorbent core comprises one or more layers.

9. The absorbent article according to claim 8, wherein the absorbent core comprises an acquisition/storage layer and a storage layer, wherein the acquisition/storage layer includes the primary water-absorbing agent and the storage layer includes the secondary water-absorbing agent, and wherein the absorbent core comprises less than about 10% by weight (of the combined weight of the primary water-absorbing agent and secondary water-absorbing agent) of fibrous cellulose material.

10. The absorbent article according to claim 1, wherein the article is an infant diaper having a first waist region, a second waist region and a crotch region therebetween, and further comprising a topsheet and a backsheet, wherein the absorbent core is present between the topsheet and backsheet, and wherein the article has a maximum dry caliper in the crotch region of about 5.5 mm or less.

11. The absorbent article according to claim 8, wherein the one or more layers have an average density greater than about 0.2 g/cm$^3$.

12. The absorbent article according to claim 1, wherein the compound is present without forming a chemical bond with the water-absorbing particles.

13. The absorbent article according to claim 1, wherein the compound is separable from the water-absorbing particles.

* * * * *